United States Patent [19]

Colebourne et al.

[11] 4,005,232

[45] Jan. 25, 1977

[54] COATINGS OF METAL PHOSPHATES ON METALS OR GLASS

[75] Inventors: Neville Colebourne; Nicholas Rolfe; Kevin Thomas McAloon, all of Runcorn, England

[73] Assignee: Imperial Chemical Industries Limited, London, England

[22] Filed: Feb. 25, 1975

[21] Appl. No.: 552,748

Related U.S. Application Data

[62] Division of Ser. No. 272,495, July 17, 1972, abandoned.

[30] Foreign Application Priority Data

Oct. 29, 1971 United Kingdom ............ 50354/71
Nov. 4, 1971 United Kingdom ............ 51293/71
Nov. 26, 1971 United Kingdom ............ 55002/71

[52] U.S. Cl. .......................... 428/35; 148/6.15 R; 148/6.15 Z; 427/106; 428/36; 428/375; 428/378; 428/379; 428/389; 428/469; 428/472; 428/539; 428/432

[51] Int. Cl.² ........................................ B32B 17/06

[58] Field of Search ..... 117/169 R, 124 B, 126 GF, 117/33.3, 124 A, 127; 148/6.15; 350/1; 428/432, 539, 469, 472, 913, 36, 35, 389, 378, 379, 375; 427/106

[56] References Cited

UNITED STATES PATENTS

| 2,843,504 | 7/1958 | Van Bakel | 428/432 |
|---|---|---|---|
| 3,023,337 | 2/1962 | Repsher | 428/432 UX |
| 3,481,758 | 12/1969 | Upton | 428/432 |
| 3,709,723 | 1/1973 | Watanabe | 148/6.15 R |
| 3,736,176 | 5/1973 | Francel | 428/432 |
| 3,853,587 | 12/1974 | Haskell | 428/539 |
| 3,853,591 | 12/1974 | Haskell | 428/539 |

OTHER PUBLICATIONS

Kirk–Othmer Encyclopedia of Chem. Tech., "Phosphoric Acids and Phosphates," vol. 15, p. 266, 1969.

*Primary Examiner*—George F. Lesmes
*Assistant Examiner*—Ellis P. Robinson
*Attorney, Agent, or Firm*—Cushman, Darby & Cushman

[57] ABSTRACT

A metal phosphate coating is applied to a glass article. A liquid composition containing at least in part an organic component and a metal compound having a metal with an atomic number of 12, 14, 20–32, 39–50, 56–80, 90 or 92 and an oxyacid of phosphorus is applied to the glass article. The liquid composition is converted to the metal phosphate coating, i.e., by air drying and/or heating, to give a coating of 0.01 to 5 microns thickness and being transparent to visible light but ultra-violet absorbing.

7 Claims, No Drawings

COATINGS OF METAL PHOSPHATES ON METALS OR GLASS

This is a division of application Ser. No. 272,495 filed July 17, 1972, now abandoned.

This invention relates to coatings on glass or metal of chemical compositions of metals and complexes isolatable therefrom, particularly coatings of compositions and complexes containing organic ligands and ligands derived from oxyacids of phosphorus of arsenic. The compositions and complexes and their preparation are described in the co-pending U.S. patent application Ser. No. 272,458 filed July 7, 1972, now abandoned of Colebourne and Rolfe, assignors to Imperial Chemical Industries Limited, which is based on U.K. Patent Applications 34012/71 and 58999/71.

Metals, for the purpose of the present specification, are defined as the elements of the periodic table of elements, having an atomic number of 12, 14, 20 to 32, 39 to 50, 56 to 80, 90 or 92. By an oxyacid of phosphorus or arsenic we mean a phosphorus or arsenic compounding containing the group of structure (1)

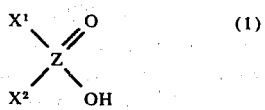

where Z is a phosphorus or arsenic atom, $X^1$ and $X^2$ are the same or different and selected from hydrogen, hydroxyl and halide, or, when Z is phosphorus, $X^2$ may have the structure (2) to provide pyrophosphate

These oxyacids and ligands derived therefrom are referred to as phosphate and arsenate: within the term are included the meta-phosphate and arsenate and pyrophosphate.

The invention has several aspects and these will be described under the following heading E. For convenience details of the compositions and complexes are also given under headings A to D.

A The compositions
B Complexes isolatable therefrom
C Methods of preparing complexes
D Properties of the complexes and their solutions
E Uses of the compositions and complexes in forming coatings
F Examples of products and processes under heading E

A THE COMPOSITIONS

Our invention uses liquid metal-containing compositions which comprise a solution, in an at least partly organic, preferably oxygen-containing, solvent, of (a) a metal compound and (b) an oxyacid of phosphorus or arsenic or a compound capable of forming such an oxyacid in the solution. These compositions are capable of decomposing on heating to a metal phosphate or arsenate.

The organic solvent is preferably selected from alcohols, esters, ketones, aldehydes, nitro compounds and ethers, especially monohydric alcohols, ROH containing 1 to 10 carbon atoms, esters of the structure $R^1COOR^2$ where R, $R^1$ and $R^2$ are alkyl groups or substituted alkyl groups containing from 1 to 10 carbon atoms each, ethers of the structure $R^1OR^2$ and ketones of the structure $R^1COR^2$, where $R^1$ and $R^2$ have the meaning ascribed above, nitro compounds of the structure $R^1NO_2$ and ethers of the structure $OR^3$ where $R^3$ is a divalent alkyl group having from 4 to 7 carbon atoms one of which may be replaced by an oxygenation. Mixtures of one or more solvents may be used. Diluents may also be present, provided they do not bring about precipitation of the components of the composition. Up to 50% of aromatic or halogenated hydrocarbon diluents may be present. The effect of including larger amounts of such diluents will be discussed in detail later.

While phosphate and arsenate are used in this specification to cover oxyacids of phosphorus or arsenic in general, orthophosphate and orthoarsenate are preferred.

The metal-containing composition may be formed by dissolving a complex of the type described in Section B of this specification in a solvent. Alternatively a metal compound and an oxyacid of phosphorus or arsenic (or a source thereof, such as the acid anhydrides or an oxyhalide) are dissolved in a solvent for at least one component and the reaction product in the presence of organic ligands. The metal compound may be a phosphate or arsenate and so provide the oxyacid of phosphorus or arsenic, in which case an additional acid may be required, e.g. hydrochloric or nitric acid.

A wide range of metal compounds may be used. Simple inorganic salts including oxides and hydroxides are suitable, such as halides, carbonate, nitrate, phosphate, perchlorate and cyanate. Sulphates may be used in some applications but they can be disadvantageous for some purposes owing to the difficulty with which they are thermally decomposed.

Also suitable are salts of organic acids such as acetates, benzoates, propionates or formates. Alkoxides are also useful.

Alternatively co-ordination complexes of the metal may be used, for example complexes having ligands derived from acetylacetone, ethylenedithiol, ethanolamine, carbon monoxide or phosphines.

Mixtures of metal salts and ligand-forming reagents may be used. Also, two or more salts or complexes of the same or different metals may be used, if desired.

The preparation of compositions containing a wide range of metals will be described in detail later.

The solvent is selected from the wide range of organic solvents which dissolve the components of the composition. Aliphatic alcohols containing 1 to 10 carbon atoms are particularly convenient, especially lower molecular weight alcohols containing 1 to 4 carbon atoms, for example methanol, ethanol, n- or iso-propanol and substituted alcohols especially methoxy- or ethoxy-ethanol. Suitable esters are ethyl acetate or carbonate. Acetyl acetone may be used. Tetrahydrofuran is the most preferred ether to use, though dioxan may also be used. Aromatic hydroxy compounds can be used, but solubility is low in such materials.

The reactants used may be brought together in any desired order, but we prefer to add the oxyacid or a precursor thereof to the metal compound dissolved or suspended in the organic solvent.

We prefer to prepare compositions in which the metal and oxyacid are present with atomic ratios of metal to phosphorus or arsenic from 1:0.1 to 1:2.9 more preferably 1:0.5 to 1:2.

The composition may be prepared over a wide range of temperatures, for example from 50° to 150° C, but generally we prefer to mix the components at temperatures below about 60° C. The process may, if desired, be carried out at pressures above normal atmospheric pressure, but it is found that, generally, if the temperature is kept below the normal boiling point of the solvent, such excess pressure is not needed.

For optimum product yield and purity all the steps in the preparation including any preparatory operations are preferably carried out under conditions in which little additional water is introduced apart from that provided by the components such as water of crystallisation from metal compounds or water from phosphoric acid. It is not essential, however, to maintain anhydrous conditions; in fact up to about 25% by weight of the composition may be water, though the precise upper limit depends on the choice of solvent and metal concentrations and is best determined by small scale trial.

Additional components such as pigments, polymers, colourants, surfactants or sources of other ions and other additives may be included in the compositions, but since the purpose of the additonal component is related generally to uses of the composition, detailed discussion will be deferred until a later section.

The liquid compositions may be converted into dry compositions by removal of the solvents, provided the compositions are maintained in an atmosphere of the solvent. Spray-drying is a convenient technique for producing solids. These may be redissolved in suitable solvents of the type described to reconstitute the liquid composition.

The solubility of our compositions in organic solvents is due to complex formation. These complexes may be isolated and their nature and typical properties will now be described.

B THE COMPLEXES

Our invention may also use metal-containing complexes in which there is associated with a metal ion one or more phosphate or arsenate ligands and one or more organic ligands, the organic ligands being derived from organic compounds containing an electron-donating oxygen atom or their thio-equivalents. The most commonly used organic compounds for this purpose are hydroxyl compounds, especially alcohols; carbonyl compounds including aldehydes, ketones and esters; nitro compounds and ethers including cyclic ethers. Of particular importance because of their ready availability are lower monohydric alcohols ROH containing 1 to 10 carbon atoms, esters of the structure $R^1COOR^2$ where R, $R^1$ and $R^2$ are alkyl groups or substituted alkyl groups containing from 1 to 10 carbon atoms each. Ethers or ketones of the structure $R^1$—O—$R^2$ or $R^1$—CO—$R^2$ nitro compounds of the formula $R^1NO_2$, where $R^1$ and $R^2$ have the meaning ascribed above, and ethers of the structure $OR^3$ where $R^3$ is a divalent alkyl group having up to 7 carbon atoms one of which may be replaced by an oxygen atom.

The complexes are difficult to characterise structurally because some of the ligands are rather labile but the evidence which will be discussed inidcates the presence of complex ions of the structure (4) in cases where the metal has a valency of $m$ and co-ordination number of 6 or more.

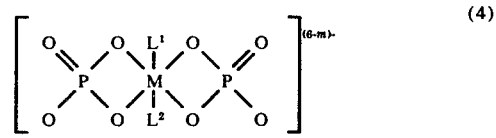

or where the coordination number is four, the equivalent complex ion is of the structure

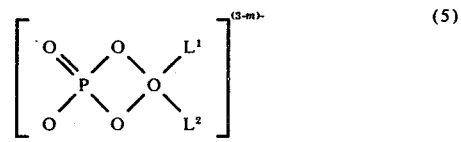

In formulae (4) and (5) $L^1$ and $L^2$ represent other ligands, at least one of which in a given ion is an organic ligand. $L^1$ and $L^2$ may be also inorganic ligands, such as halide, sulphate, nitrate or thiocyanate, when corresponding adjustment of the total valency of the ion will have to be made. Complexes may contain more than one unit of structure (4 or 5) linked together through hydrogen bonding of organic ligands $L^1$ and $L^2$: also at least one but not all of ligand pairs $L^1$ and $L^2$ may be replaced by bidentate groups such as phosphate groups. Such an ion is difficult to represent in two dimensions but a complicated structure of this type containing additional phosphate ligands accounts for the analyses of certain complexes of the invention containing trivalent metals having a metal to phosphate ratio in the range 1:1 to 1:2.9.

Q is a metal of atomic number 12, 14, 20–32, 39–50, 57–80, 90 or 92, having a valency $m$ and a co-ordination number of 4.

The counter ion associated wth the anions described above may be selected from a wide range of cations but is usually hydrogen ($H^+$) or $M^{m+}$ or $Q^{m+}$.

The complexes may be characterised in several further ways. Heating the solid decomposes it to a metal phosphate and a distillate is obtained which consists mainly of an organic compound corresponding to the co-ordinated organic liquid.

Proton magnetic resonance studies on alcoholic solutions of the complexes show a shift of resonance to a field high of the usual proton resonance range and the resonance is broadened. For example an iron complex in methanol shifts the resonance 30 ppm high. That the complexes are not strongly bound together is indicated by the observation of only a single signal for solvent and ligand methanol, suggesting rapid exchange.

Infra-red or laser-Raman spectroscopy may be used to characterize the complex and to identify the presence of phosphate groups (about 900–925 $cm^{-1}$ and 1088 $cm^{-1}$) and the organic ligand. Compared with the organic compound from which the ligand is derived the peaks in the spectrum of the complex often show a shift (in one or other direction) of 3–12 $cm^{-1}$, suggesting weak coupling.

Ultra-violet spectroscopy may be used to characterise the environment of the metal, conveniently by evaporating a solution of the complex on a quartz plate and measuring ultra-violet transmission over the range 200 to 450 millimicrons. In the examples at the end of this specification ultra-violet characteristics of complexes of a number of metals will be described in detail.

C METHODS OF PREPARING COMPLEXES

Several methods will be described, all of which have in common the feature of bringing together, in a solvent for at least one component or the product complex, a source of an oxyacid of phosphorus or arsenic, a source of metal ions and a source of organic ligands. Conveniently the source of organic ligands is the solvent or part of the solvent. The differences between the several processes described are mainly in connection with the method of isolating the product complex from the composition. For any given solvent or mixture of solvents, the process conditions can be adjusted either to maintain the complex in solution, or to precipitate it, according to whether its solubility product is exceeded. Precipitation can be achieved, for example, by selection of the solvent, by concentration, by altering the temperature and/or pressure, or by addition of a further component in which the complex has a low solubility. For some purposes however such isolation is not necessary, for the compositions may be used as prepared. Since the organic ligands are usually rather labile, if the isolated complex is to be stored, it should be maintained in an atmosphere of the ligand source, i.e. the organic solvent which provides the ligand.

According to a first process for preparing a complex for use in our invention, an oxyacid of phosphorus or arsenic or a source thereof, a metal compound and a source of organic ligands are brought together in an organic medium which is capable of dissolving the components but in which the solubility product of the resulting complex is exceeded. The complex phosphate or arsenate produced may be isolated for example by filtration, decanting off the remaining liquid or by centrifuging. The product may be dissolved in another solvent, e.g. an alcohol, for use.

Suitable organic media for this process include ethers, preferably cyclic ethers, esters, alcohols, ketones, nitro-compounds, amide, carbonates, sulphones, sulphoxides and mixtures of such solvents. Examples of such suitable solvents are tetrahydrofuran, dimethyl sulphoxide, ethylene carbonate, propylene carbonate, acetone, methyl ethyl ketone, methyl acetate, n-propyl alcohol, n-butyl alcohol, ethyl acetate, nitromethane, ethyl acrylate and diethyl carbonate.

The reactants used may be brought together in any desired order, but we prefer to add the oxyacid, or a precursor thereof, to the metal compound dissolved in the organic medium.

In this case the oxyacid, or precursor thereof is added directly or in solution to a solution of the metal compound, to precipitate the complex.

According to a second process for preparing a complex for use in our invention, a metal compound, a source of organic ligands and the oxyacid of phosphorus or arsenic or precursor thereof, are dissolved in a solvent for the components and the reaction product, then the complex is separated by adding a phase separator to the reaction mixture.

The phase separator is an organic substance which is miscible with the solvent used but in the presence of which the solubility product of the complex is exceeded. Thus the complex separates out as a solid or as an oil.

The phase separator is preferably a substance having a low dielectric constant, especially a dielectric constant from 2 to 11. Most preferred phase separators have a low co-ordinating power for the metal of the compounds used in the process. It is usual for the phase separator to be a liquid at the temperature at which the process is carried out; preferred liquids are hydrocarbons and halogenated derivatives, for example methylene chloride, trichloroethylene, carbon tetrachloride, chloroform, ethylene dichloride, methyl chloroform, chlorobenzene, toluene, xylene, benzene or $C_6$ to $C_{12}$ aliphatic hydrocarbons. Certain organic liquids can act as co-ordinating ligands or as phase separators. For example, in the presence of methanol as principal solvent and organic ligand source, diethyl ether may act as a phase separator. In the absence of a solvent of such high co-ordinating power as methanol, diethyl ether may act as a co-ordinating solvent. Best results therefore require a certain amount of straightforward trial. Some degree of concentration of the solution may be required e.g. evaporation under low pressure, before the phase separator is added.

Reaction conditions of temperature, pressure and metal to phosphorus ratio are generally as described above in connection with the compositions.

D PROPERTIES OF COMPOSITIONS, COMPLEXES AND THEIR SOLUTIONS

A particular property of these materials which makes them useful for many technical purposes is their ability to decompose to mainly amorphous metal phosphates which are highly insoluble in solvents for the original composition. In essence the composition is heated to remove any solvent which remains and also the co-ordinated organic ligands which are responsible for conferring solubility on the complex. Further heating may be advantageous in removing bound water to give greater insolubility.

When a complex has been isolated, it is preferably dissolved as prepared, or in at least partly purified form, in a suitable solvent before decomposition. A suitable solvent may conveniently be selected from the organic co-ordinating solvents used in the preparation of a composition or complex. Some water may be present, provided the complex remains in solution.

Useful protic solvents are for example, methanol, ethanol, cyclohexanol, n-propanol, benzyl alcohol and especially methanol. Higher alcohols, substituted alcohols, polyfunctional alcohols and aromatic alcohols, for example butanol, 2-methoxy-ethanol, 2-ethoxy-ethanol, 2-butoxy-ethanol, trichloroethanol, trifluoro-ethanol, bromomethanol, ethylene glycol, glycerol and cresol may also be used as solvents. Aprotic solvents may also be used, for example tetrahydrofuran, N,N-dimethyl formamide, N-methyl pyrrolidone, N,N-dimethyl acetamide, dimethyl sulphoxide, ethylene carbonate, propylene carbonate, acetone, methyl ethyl ketone, ethyl acetate, methyl acetate and nitromethane. Especially useful solvent mixtures are derived from methanol or ethanol and a chlorinated hydrocarbon, for example, chloroform, methylene chloride, ethylene dichloride and trichloroethylene; from methanol and methyl ethyl ketone or tetrahydrofuran; from methanol and dimethyl formamide; from methanol and chloral hydrate and from methoxy- or ethoxy-ethanol and toluene.

Decomposition of the composition is preferably carried out by heating or by air-drying at room temperature, optionally under reduced pressure.

Heating may be carried out at comparatively low temperatures, for example from 30° to 120° C, to form the phosphate or arsenate of the metal. Stronger heating, for example at temperatures greater than 150° C up to 1000° C, can produce a phosphate or arsenate of the metal of somewhat different composition, due it is believed, to condensation and cross-lining. The duration of heating varies over a wide range depending upon the particular composition and the desired end-product and is typically from practically instantaneous, as when a solution is sprayed onto a hot surface, up to 100 hours.

E USES OF COMPOSITIONS AND COMPLEXES IN FORMING COATINGS

A composition, including a complex or a solution of a complex of the type described, may be used to coat glass or metal substrates by applying it to the substrate and subsequently allowing it or causing it to decompose to form an insoluble coating of the phosphate or arsenate of the metal the coating being in the range 0.01 to 5 microns thick. The substrate may take up a variety of shapes, e.g. fibre, filament, sheet, granule, powder or cenospheres. The substrate may be coated with or impregnated with solution. The coatings are usually non-crystalline. A complex metal phosphate for use in the invention can be used to produce heat-stable, inert, transparent, hard films of a phosphate of a metal, especially films of the phosphates of iron, titanium, vanadium or chromium. Coatings of phosphate may be prepared in relatively thick layers for each application of coating solution. Ferric phosphate and titanium phosphate and mixtures of the two have useful ultra-violet radiation absorbing properties; chromium phosphate is useful when coated onto glass to enhance the water and alkali-resistance of the glass. We have found that coatings of thickness in the range 0.01 to 3 microns, preferably 0.2 to 2.5 microns give the best results. Thick coatings may be produced by repeated coatings, with or without conversion to phosphate between each stage. Mixtures of two or more metals may be present in the compositions. Aluminium compounds may also be present.

A convenient method for applying the coating comprises dip-coating, spraying, powder-, roller- or brush-coating the substrate to be coated with a composition or solution of complex according to the invention, removing part or all of any organic solvent, then decomposing the complex to yield a phosphate, at a temperature from room temperature up to 1000° C or such lower temperature than 1000° C that is set by the maximum temperature which the substrate to be coated can withstand without damage or loss of useful properties. Of course, if at the same time as decomposing the phosphate thermal modification of the substrate is planned, then the temperature may be set accordingly.

The coating solution may include additional components, for example materials which will aid the further processing of the solutions or desirably affect the properties of the coatings formed from the solutions. Thus organic materials, especially polymers or monomers, may be dissolved in the complex solution given an appropriate solvent. Examples of suitable polymers include diene polymers, acetylene polymers, vinyl and vinylidene polymers, e.g. acrylic acid and methacrylic polymers, acrylate and methacrylate polymers, polyacrylonitrile, polyethers, polysulphones, formaldehyde resins, polyesters, polycarbonates, polyamides, polyureas and polyurethanes, natural polymers and modified natural polymers and polysiloxanes. Copolymers or terpolymers of the monomers of the aforementioned may also be used. In some cases it will be convenient to dissolve the corresponding monomer in the complex solution and polymerise it later, for example simultaneously with the thermal decomposition of the complex. It will be understood that a suitable solvent of solvent mixture has to be chosen which will dissolve both the complex and the polymer.

Additional components, for example pigments, colourants, surfactants, plasticisers, antioxidants, heat stabilisers, ultra-violet stabilisers, or fillers such as metal powders may also be dispersed in the composition. Additional compounds which may be introduced include materials which can control the chemical or physical nature of the solid phase of metal phosphate which is produced from the solution. Thus a boric acid ester or ether or a silicic acid ester or ether (for example methyl borate, trimethoxy boroxine or ethyl silicate) may be introduced to suppress the crystallisation of the metal phosphate.

The ultra-violet absorption properties of the coatings may be enhanced by introducing a compound of another metal. It is especially preferred to incorporate, for this purpose, a compound of chromium, iron, titanium or of a manganese which is soluble in the particular solvent used. Thus, for example manganese(II), iron(III), or titanium(III) or (IV) or chromium(III) may be incorporated in the solution from which the coating is formed.

The ultra-violet absorption properties of the coating may also be enhanced by introduction of organic compounds which themselves absorb in the ultra-violet, for example benzophenones and benzotriazoles. When the solubility of the organic compound allows, it may be dissolved in the solution from which the coating is formed; alternatively the organic compound may be introduced in particulate form by slurrying with the solution of the complex. If desired, both transition metals and organic compounds may be introduced into a single coating.

The chemical resistance of the coatings may similarly be enhanced by the introduction of compounds of other metals for example tin or calcium or a boron compound. Aluminium phosphate precursors may also be present.

The coatings may be used to modify the surface energy of the substrate to give hydrophilic or hydrophobic coatings.

The refractive index of the coatings may be modified as desired by the incorporation of metal compounds or organic polymers.

In certain applications particulate solids may usefully be dispersed in the solutions of the complex as for example, refractory materials such as silica, or metal oxides including titania and zirconia may be so dispersed to produce, on decomposition of the complex, a metal phosphate coating containing refractory materials. Thus the inclusion of graphite is useful in producing an electrically-conducting metal phosphate. Solid-phase lubricants such as graphite, molybdenum sulphide, poly(carbon monofluoride) and polytetrafluoroethylene, may be present.

E(i) COATINGS ON GLASS SUBSTRATES

Glass coated with metal phosphate, especially iron phosphate has a wide variety of applications but is especially advantageous in light control on sheet glass, lamp bulbs or tubes or other transparent or translucent articles. For example, the emission of ultra-violet radiation from fluorescent lamps or tubes is undesirable; in some circumstances the radiation may be damaging to the eyes and may also cause degradation of plastics materials used as light-diffusing shields for the fluorescent tubes. An iron or titanium phosphate coating is advantageous in reducing the transmission of ultra-violet radiation.

The coating of transition metal phosphate may be applied to the inside and/or the outside surface of the glass (including quartz) envelope. The resistance of the coatings to attack by alkali-metal vapours, mercury vapour and halogens and compounds thereof is also advantageous in providing a resistant coating for the inner surface of glass or quartz bulbs or tubes for use in lighting equipment.

Glass coated with an iron phosphate also finds application as window glass and glass containers for use in circumstances where it is desired to reduce the degree of transmission of ultra-violet visible and infra-red radiation, for example to minimise degradation of materials exposed to the transmitted radiation, or to reduce heating or glare.

The coating may be applied to glass sheet to improve strength and abrasion resistance. Glass fibres may also be coated for this purpose, either as a temporary or as a permanent coating. The coating may be applied to freshly-spun fibre or to staple fibre, with or without removing sizes.

The chemical resistance of glass is also assisted, if appropriate phosphates are selected, depending upon the intended application. The surface energy of glass is altered by the coating and is found to give antimisting properties. The coatings also assist in smoothing out surface irregularities and may at least partly replace polishing in some circumstances. The visual appearance of glass may be altered e.g. by colouring or modifying refractive index. For this purpose dyes or pigments may be included. The coatings may be used as anchor coatings for resins, especially on glass fibres. Glass fibres may be coated in the form of mats, cloth or blankets, as a substitute for conventional sizes for use in resin reinforcement, electrical and heat insulation.

The complex phosphates produced have semiconducting properites in many cases. For use in applications where anti-static properties are desirable it is preferred that the bulk resistivity of the coating be not more than $10^{10}$ ohm cm. A bulk resistivity of not more than $10^8$ ohm cm is especially preferred, for example in the range $10^4$ to $10^6$ ohm cm. In order to achieve a low bulk resistivity it is preferred to carry out the decomposition of the complex at a temperature not above 240° C, most preferably at a temperature below 200° C (for example in the range 120° to 190° C). In some cases however, especially when mixed phosphates are used, higher temperatures may be used with advantage.

E(ii) COATINGS ON METAL SUBSTRATES

Coatings may be provided on metals using the solutions, additives and coating techniques described above.

The metal phosphate provides a coating with low electrical conductivity and limited permeability to oxygen and water. Therefore the coatings offer useful anti-corrosion properties especially for use on ferrous metals. The coatings themselves are not so susceptible to atmospheric attack as the conventional, thicker, crystalline phosphate coatings used for metal treatment. The adhesion of conventional resinous surface coatings, including paints, to the phosphate or arsenate coatings is good. Coatings can be applied to a wide range of shaped metal articles including sheet, foil, wire, rod, bar strip or tube materials by dip or spray-coating techniques. Iron and steel are very suitable metals for this treatment, either as a temporary or permanent protective coating.

The coating may serve to reduce wear or act as a lubricant. This may be in the short term as in forming operations, or in the longer term up to the life of the article. In forming operations the coating assists in wire-drawing, sheet rolling or pressing, including deep drawing, extrusion and other high-stress operations involving the contact or rubbing of surfaces. Similarly a more permanent application is in coating nuts and bolts to aid easy undoing, especially where the metal is prone to binding or galling as in the case of aluminium or titanium. Polymeric materials may be added to the composition to provide a single coating treatment.

In a wide range of metal-treating operations our coatings may be used in a pretreatment stage. They serve as primers in coating operations, e.g. before painting, printing, enamelling or plastic coating. They also may be used as binders for particulate coatings including, for example, pigments, solid lubricants and metal oxides or powders. The finished, treated, metal article may be provided with a coating to improve durability, corrosion or abrasion resistance or appearance. Thus rough surfaces may be smoothed, or anodised surfaces may be protected from abrasion.

It is also useful to apply our coatings to aluminium to aid adhesion of further coating materials in addition to or instead of anodising treatments.

Our coatings also assist in maintaining decorative metal finishes by reducing atmospheric attack. Stainless steel, galvanised steel, copper, bronze, brass, tantalum, zirconium and titanium may be coated to extend the life of the decorative finish.

The coatings may also be used as binders for solid-phase lubricants used in forming operations such as drawing, rolling or extrusion.

The invention is illustrated but not limited by the following Examples:

EXAMPLE 1

A filtered 23% by weight solution of anhydrous ferric chloride in "Analar" grade methanol (255 ml) was treated at room temperature with 20.7 ml of 88% orthophosphoric acid. The mixture was then stripped of excess methanol (52 ml) by means of a rotary evaporator, and the residual liquor stripped further under dynamic vacuum. The distillate from this stripping contained a large quantity of hydrogen chloride. The syrupy concentrate was then treated at room temperature with 1 liter of methylene chloride and shaken vigorously. The white solid complex derivative obtained at this stage was filtered off and washed free of soluble iron (as $HFeCl_4$) with methylene chloride. The residual solid was dissolved in 250 ml methanol to give a light brown solution. After removal by distillation of 170 ml methanol the viscous residual was analysed and found to contain, by weight, 12.25% Fe and 11.7% P corresponding an atomic ratio Fe/P = 1/1.7.

This residual solution was diluted with methanol to give a solution containing 6.0% by weight of iron as Fe. A portion of the resulting solution (Solution A) was used to coat a "Spectrosil" silica slide by a dipping procedure, the slide being withdrawn from the solution (at 20° C) at the rate of three inches per minute. Excess methanol was removed by drying in a stream of nitrogen for ten minutes at ambient temperature. The coated slide was then "cured" in an oven at 120° C for 30 minutes. The thickness of the final coating (measured electrochemically) was 0.8 micron. The U.V. spectrum of the resulting iron phosphate coating was measured using a "Unicam" SP800 spectrophotometer and the results obtained were as follows:

| wavelength (millimicrons) | % transmittance |
| --- | --- |
| 400 | 70 |
| 350 | 18 |
| 340 | 8.5 |
| 330 | 2.8 |
| 325 | 0 |

EXAMPLE 2

A portion of Solution A (as described in Example 1) was further diluted with methanol to give a solution (Solution B) containing 2.0% by weight of iron as Fe. Solution B was used to coat a Spectrosil slide using the method described in Example 1. The final iron phosphate coating (after curing) was 0.24 micron in thickness and its U.V. spectrum was as follows:

| wavelength (millimicrons) | % transmittance |
| --- | --- |
| 400 | 95 |
| 325 | 55 |
| 310 | 18 |
| 300 | 4.8 |
| 290 | 0.5 |

EXAMPLE 3

A complex iron derivative was prepared by the method described in Example 1, the dilution with methanol being such that the concentration of iron (as Fe) in the final methanol solution (Solution C) was 4.3% by weight.

Solution C was used to coat one-half of the length of the outside surface of an 8-watt glass fluorescent tube (Atlas-Thorn). The initial stage of the coating was carried out at ambient temperature, the tube being withdrawn from the coating solution at the rate of nine inches per minute. After drying under nitrogen at ambient temperature the coating was curred at 120° C for 1 hour. This procedure of coating and curing was repeated to give a final coating 0.5 micron in thickness.

The emission from the lamp was measured using a monochromator and photo-cell over the range of wavelengths 250 to 400 m$\mu$. The uncoated half of the tube showed strong emission at 313 and 365 m$\mu$ due to the mercury discharge. The coated half of the tube showed no emission below 350 m$\mu$ (i.e. the intensity of the emission at 313 m$\mu$ was reduced to a level not more than 1% of that of the uncoated half of the tube) and the emission at 365 m$\mu$ was reduced to 70% of that of the uncoated tube. The emission of the coated half at 400 m$\mu$ was 90% of that of the uncoated half and the emission in the visible region appeared unaffected to the eye.

EXAMPLE 4

A solution of the complex iron derivative was prepared by the method described in Example 1, the dilution with methanol being such that the concentration of iron (as Fe) in the final solution (Solution D) was 1.0% by weight.

A solution containing manganese (Solution B) was prepared by dissolving 0.0625 g $MnCl_2.4H_2O$ in a 50 g portion of Solution D.

Another solution containing manganese (Solution F) was prepared by dissolving 0.313 g $MnCl_2.4H_2O$ in another 50 g portion of Solution D.

Solutions D, E and F were used to coat Spectrosil slides by a method similar to that described in Example 1. Three successive coatings wereapplied in each case, the temperature of curing being 300° C and the thickness of the coating finally obtained was 0.2 micron. The absorption spectra of the coatings were as follows:

| solution used for coating | wavelength (millimicrons) | % transmittance |
| --- | --- | --- |
| D | 350 | 75 |
|   | 325 | 52 |
|   | 300 | 20 |
|   | 250 | 5 |
| E | 350 | 61 |
|   | 325 | 39 |
|   | 300 | 19 |
|   | 250 | 3 |
| F | 350 | 58 |
|   | 325 | 32 |
|   | 300 | 9 |
|   | 250 | 0 |

EXAMPLE 5

A solution of an iron phosphate complex in methanol was prepared by the method described in Example 1, the final dilution being such that the concentration of iron (as Fe) was 2.3% by weight. A portion of this solution was used to coat a specimen of quartz, the surface coated having the dimensions 1.0 cm × 1.0 cm. After removal of excess methanol in a stream of nitrogen at ambient temperature the coating was cured at 100° C to yield a layer of an iron phosphate 0.4 micron thick. The bulk resistivity of the coating, measured using a Vibron 33C-2 instrument (E.I.L. Ltd.) was 4.2 × $10^6$ ohm cm.

The coating procedure was repeated with similar quartz specimens, using a different temperature of curing in each case. The results obtained were as follows:

| thickness of coating micron | "curing" temperature ° C | bulk resistivity ohm cm |
| --- | --- | --- |
| 0.7 | 130 | 5.0 × $10^5$ |
| 0.4 | 160 | 5.0 × $10^5$ |
| 0.7 | 190 | 8.0 × $10^5$ |
| 0.6 | 220 | 9.8 × $10^7$ |

-continued

| thickness of coating micron | "curing" temperature ° C | bulk resistivity ohm cm |
|---|---|---|
| 0.6 | 250 | $8.8 \times 10^8$ |

EXAMPLE 6

A filtered solution of anhydrous ferric chloride (350g) in Analar grade methanol (255 ml) was treated at room temperature with 131 ml of 88% orthophosphoric acid. The mixture was then stripped of excess methanol by means of a rotary evaporator, and the residual liquor stripped further under dynamic vacuum. The distillate from this stripping contained a large quantity of hydrogen chloride. The syrupy concentrate was then treated at room temperature with three times its volume of methylene chloride and shaken vigorously. The white solid complex derivative obtained at this stage was filtered of and washed free of soluble iron (as $HFeCl_4$) with methylene chloride. The residual solid was dissolved in methanol to give a viscous solution (Solution G) containing, by weight, 12.0% Fe and 14.0% P corresponding to an atomic ratio $Fe/P = 1/2.1$.

A "Pyrex" glass capillary tube of 0.185 cm bore was clamped in a vertical position. A length of copper wire (16 gauge, 0.166 cm diameter) was wetted with Solution G by dipping into a portion thereof and was then inserted upwardly into the capillary tube and clamped in such a position that the upper end of the copper wire was just below the upper end of the capillary tube. A 0.5 ml portion of Solution G was then introduced into the upper end of the capillary tube in such a way that the solution covered the upper end of the copper wire and also formed a layer between the inner wall of the capillary tube and a short portion of the copper wire.

Methanol was allowed to evaporate from this solution for 20 minutes at ambient temperature and the assembly was then cured by heating at 200° C for 2 hours, thereby producing a glass-copper seal comprising an iron phosphate.

Glass-metal seals were produced in the same manner using (a) titanium wire, (b) zirconium wire and (c) tantalum wire. In each case the diameter of the wire was 0.166 cm and the bore of the glass capillary tube was 0.185 cm.

A glass-bronze seal was produced in a similar manner except that the bore of the glass capillary tube was 0.195 cm, the diameter of the bronze wire being 0.166 cm.

EXAMPLE 7

A filtered solution of anhydrous ferric chloride (350g) in Analar grade methanol (450ml) was treated at room temperature with 131ml of 88% orthophosphoric acid. The mixture was then stripped of excess methanol by means of a rotary evaporator, and the residual liquor stripped further under dynamic vacuum. The distillate from this stripping contained a large quantity of hydrogen chloride. The syrupy concentrate was then treated at room temperature with three times its own volume of methylene chloride and shaken vigorously. The white solid complex derivative obtained at this stage was filtered off and washed free of soluble iron (as $HFeCl_4$) with methylene chloride. 700 grams of the residual solid were dissolved in 500ml methanol and the remaining methylene chloride was removed by evaporation at 55° C for 30 minutes. The viscous residual solution (Solution H) was analysed and found to contain, by weight, 11.6% Fe and 12.8% P.

A portion of Solution H was diluted with methanol to give a solution (Solution I) containing 2.9% Fe.

A series of sample panels of mild steel were degreased by treatment with trichloroethylene vapour and were then coated with Solution I by a dipping procedure. Excess methanol was removed by drying in a stream of nitrogen for 10 minutes at ambient temperature. The coated sheets were then cured in an oven at 120° C for 30 minutes. The thickness of the resulting iron phosphate coating (measured electromechanically) was 0.5 micron.

The coated panels were then further coated with paint by being dipped into a trichloroethylene-based grey paint under standard conditions.

For purposes of comparison, similar mild steel panels were degreased and then coated with paint under the same conditions, the stage of coating with iron phosphate being omitted.

One panel of each series was cross-cut while a second panel of each series was tested with the paint film unbroken. The resistance of these panels to salt spray was assessed by spraying a 5% (by weight) sodium chloride solution on to the panels continuously for 8 days. In all cases the adhesion was assessed at the end of test period; in the case of cross-cut panels the extent of blistering and "lifting" of the paint film and the spread of corrosion from the cut were assessed.

The results are expressed in the following Table on a scale from 1 to 10, where 1 represents "severe corrosion and loss of adhesion" and 10 represents "no corrosion and no loss of adhesion".

|  |  | pre-coated with iron phosphate | no iron phosphate coating |
|---|---|---|---|
| Cross-Cut Panels | adhesion after test | 9 | 1 |
|  | blistering and "lifting" | 7 | 4 |
|  | spread from cut | 8 | 4 |
| Non Cross-Cut Panels | (adhesion after test | 6 | 1 |

EXAMPLE 8

A filtered solution of anhydrous ferric chloride (70g) in Analar grade methanol (90ml) was treated at room temperature with 26.2ml of 88% orthophosphonic acid. The mixture was then stripped of excess methanol by means of a rotary evaporator, and the residual liquor stripped further under dynamic vacuum. The distillate from this stripping contained a large quantity of hydrogen chloride. The syrupy concentrate was then treated at room temperature with three times its own volume of methylene chloride and shaken vigorously. The white solid complex derivative obtained at this stage was filtered off and washed free of soluble iron (as $HFeCl_4$) with methylene chloride. The residual solid was dissolved in 100ml methanol and the remaining methylene chloride was removed by evaporation at 55° C for 45 minutes. The viscous residual solution (Solution J) was analysed and found to contain, by weight, 6.0% Fe and 7.8% P.

A portion of Solution J was diluted with methanol to give a solution (Solution K) containing, by weight, 4.4% Fe.

Stainless steel samples (1 inch × 1 inch × ¼ inch) were coated with Solution K using a dipping technique. Excess methanol was removed by drying in a stream of nitrogen at ambient temperature for 30 minutes and the coated samples were then cured at 250° C for 1 hour. The dipping and curing procedure was repeated a further three times and the thickness of the final iron phosphate coating was 2.8 microns.

The coated samples were aluminised using an evaporation technique thereby providing electrodes for measurement of the resistivity and capacitance of the coatings. The average A.C. bulk resistivity was $3.0 \times 10^8$ ohm cm and the average capacitance was also measured, corresponding to a dielectric constant of 7.1.

What we claim is:

1. A coated glass article comprising a glass substrate and a coating thereon which has a thickness of 0.01 to 5 microns and is transparent to visible light but ultraviolet light absorbing, said coating being identifiable as the dried residue of a liquid coating composition containing an organic component and a solution of a metal phosphate compound wherein the metal of the compound is selected from the group consisting of iron, titanium, a mixture of iron and titanium and a mixture of iron and chromium, and wherein the phosphate of the compound is an oxyacid of phosphorus, or a compound capable of forming such an oxyacid in the solution of the said compound, the oxyacid being an ortho- or meta-acid of the structure (1)

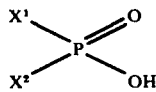

where $X^1$ and $X^2$ are the same or different and are selected from hydrogen, hydroxyl, halide or which may have the structure (2) to provide pyrophosphoric acid

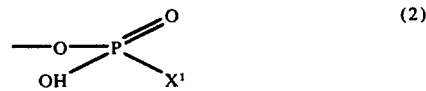

2. The coated article of claim 1 in which at least 75% by weight of the said composition is the organic component.

3. The coated article of claim 10 in which the oxyacid of phosphorus is orthophosphoric acid.

4. The coated article of claim 3 in which the said organic component is selected from alcohols, esters, ketones, aldehydes, ethers and nitro compounds or a mixture of two or more of such components.

5. The coated article of claim 4 in which the organic component is:
   a. a monohydric alcohol of the structure ROH,
   b. an ester of the structure $R^1COOR^2$ or
   c. an ether of the structure $R^1OR^2$ or a cyclic ether of the structure $R^3O$,
   d. a ketone of the structure $R^1COR^2$,
   e. a nitro compound of the structure $R^1NO_2$, where R, $R^1$ and $R^2$ are alkyl (including cyclic alkyl) groups or substituted alkyl groups containing from 1 to 10 carbon atoms and $R^3$ is a divalent alkyl group containing from 4 to 7 carbon atoms, one of which may be replaced by an oxygen atom, or mixtures of one of more of such components.

6. The coated article of claim 15 in which the atomic ratio of metal-to-phosphorus is in the range 1:0.5 to 1:2.

7. The coated article of claim 10 in which the glass article is in the form of a film, filament, sheet, tube, bulb or bottle.

* * * * *